(12) United States Patent
Visser et al.

(10) Patent No.: US 11,986,793 B2
(45) Date of Patent: May 21, 2024

(54) UPGRADING OF A RAW BLEND INTO A DIESEL FUEL SUBSTITUTE: POLY(DIMETHOXYMETHANE)

(71) Applicant: GAS TECHNOLOGIES LLC, Walloon Lake, MI (US)

(72) Inventors: Evan Visser, Spring, TX (US); Walter Breidenstein, Boyne Falls, MI (US)

(73) Assignee: Gas Technologies LLC, Walloon Lake, MI (US)

( * ) Notice: Subject to any disclaimer, the term of this patent is extended or adjusted under 35 U.S.C. 154(b) by 0 days.

(21) Appl. No.: 17/459,038

(22) Filed: Aug. 27, 2021

(65) Prior Publication Data

US 2021/0387157 A1 Dec. 16, 2021

Related U.S. Application Data

(62) Division of application No. 16/434,318, filed on Jun. 7, 2019, now Pat. No. 11,103,849, which is a division
(Continued)

(51) Int. Cl.
*B01J 19/24* (2006.01)
*B01D 3/00* (2006.01)
(Continued)

(52) U.S. Cl.
CPC ............ *B01J 19/245* (2013.01); *B01D 3/009* (2013.01); *B01D 3/143* (2013.01); *B64C 27/12* (2013.01);
(Continued)

(58) Field of Classification Search
CPC ........ B01J 19/245; B01D 3/143; B01D 3/009; C07C 41/51; C07C 41/58
See application file for complete search history.

(56) References Cited

U.S. PATENT DOCUMENTS

| 5,959,156 A | 9/1999 | Hagen et al. |
| 6,265,528 B1 | 7/2001 | Hagen et al. |

(Continued)

FOREIGN PATENT DOCUMENTS

| CN | 104003855 A | 8/2014 |
| CN | 104447240 A | 3/2015 |
| WO | 2015/142727 A1 | 9/2015 |

OTHER PUBLICATIONS

Burger, J. et al., "Poly(oxymethylene) dimethyl ethers as components of tailored diesel fuel,," Properties, synthesis and purification concepts, Fuel 89 (2010), pp. 3314-3319.
(Continued)

*Primary Examiner* — Lessanework Seifu
(74) *Attorney, Agent, or Firm* — Brooks Kushman P.C.

(57) ABSTRACT

A method for forming poly(dimethoxymethane) includes a step of separating a formaldehyde-containing blend into a first bottom stream and a first top stream. The first formaldehyde-containing blend includes methanol, formaldehyde, and water while the first bottom stream includes water. The first top stream includes dimethoxymethane that is produced from the reaction between methanol and formaldehyde. The first top stream is separated into a second bottom stream and a second top stream. The second bottom stream includes poly(dimethoxymethane) while the second top stream includes dimethoxymethane, methanol, and ethanol. The second top stream is separated into a third bottom stream and a third top stream. Third bottom stream includes methanol and ethanol while the third top stream includes dimethoxymethane. The third top steam can be recycled to form additional poly(dimethoxymethane). A system that implements the method is also provided.

12 Claims, 7 Drawing Sheets

Related U.S. Application Data of application No. 15/693,991, filed on Sep. 1, 2017, now Pat. No. 10,322,397.

(51) Int. Cl.

| | | |
|---|---|---|
| *B01D 3/14* | (2006.01) | |
| *B64C 27/12* | (2006.01) | |
| *C07C 41/56* | (2006.01) | |
| *C07C 41/58* | (2006.01) | |
| *C10G 5/06* | (2006.01) | |
| *C10L 1/02* | (2006.01) | |
| *F16H 57/00* | (2012.01) | |
| *F16H 57/025* | (2012.01) | |
| *F16H 57/04* | (2010.01) | |
| *F16H 57/02* | (2012.01) | |

(52) U.S. Cl.
CPC .............. *C07C 41/56* (2013.01); *C07C 41/58* (2013.01); *C10G 5/06* (2013.01); *C10L 1/026* (2013.01); *F16H 57/0025* (2013.01); *F16H 57/025* (2013.01); *F16H 57/0424* (2013.01); *F16H 2057/02043* (2013.01)

(56) References Cited

U.S. PATENT DOCUMENTS

| | | |
|---|---|---|
| 6,350,919 B1 | 2/2002 | Hagen et al. |
| 7,456,327 B2 | 11/2008 | Pawlak et al. |
| 7,578,981 B2 | 8/2009 | Pawlak et al. |
| 7,642,293 B2 | 1/2010 | Pawlak et al. |
| 7,687,669 B2 | 3/2010 | Pawlak et al. |
| 7,879,296 B2 | 2/2011 | Pawlak et al. |
| 7,910,787 B2 | 3/2011 | Pawlak et al. |
| 8,193,254 B2 | 6/2012 | Pawlak et al. |
| 8,202,916 B2 | 6/2012 | Pawlak et al. |
| 8,293,186 B2 | 10/2012 | Pawlak et al. |
| 9,255,051 B2 | 2/2016 | Pawlak et al. |
| 2007/0260094 A1 | 11/2007 | Schelling |
| 2008/0221368 A1 | 9/2008 | Stroefer et al. |
| 2015/0089862 A1 | 4/2015 | Gaffney et al. |
| 2017/0081602 A1 | 3/2017 | Gaffney et al. |

OTHER PUBLICATIONS

Cusack, R., "Rethink your liquid-liquid separations," Hydrocarbon Processing, Jun. 2009, pp. 53-60.

Search & Examination Report dated Mar. 8, 2019 for British Appn. No. GB1813521.0, 9 pgs.

Weissermel, L. et al., Industrial Organic Chemistry, Third, Complete Revised Editio, 1997, 481 pgs.

Zheng, Y. et al., "Synthesis of polyoxymethylene dimethyl ethers over exchange resin," Alternative Fuel and Enabling Technologies IV, 24 pgs.

Office Action dated Sep. 7, 2018 for U.S. Appl. No. 15/693,991, filed Sep. 1, 2017, 17 pgs.

Non-Final Office Action dated Dec. 20, 2019 for U.S. Appl. No. 16/434,318, filed Jun. 7, 2019, 16 pgs.

Final Office Action dated Jul. 27, 2020 for U.S. Appl. No. 16/434,318, filed Jun. 7, 2019, 10 pgs.

Examination Report dtd Nov. 24, 2023 for CA Appn. 3,118,278, 4 pgs.

Table 1.

| Mole Fraction | 100 | 101 | 102 | 103 | 104 | 201 | 202 | 301 | 302 | 401 | 501 | 601 | 701 |
|---|---|---|---|---|---|---|---|---|---|---|---|---|---|
| ETHANOL | 0.0340891 | 0.0340891 | 0.0340891 | 0.0340849 | 0.0305795 | 0.0637011 | 0.0326807 | 0.0103107 | 0.0103152 | 0.0332971 | 0.0136518 | 2.90E-10 | 0.0665943 |
| H2O | 0.4065984 | 0.4066009 | 0.4069308 | 0.4250591 | 0.4069922 | 0.1017076 | 0.0522326 | 0.9587153 | 0.9580937 | 1.00E-30 | 1.63E-13 | 0 | 0 |
| FORMALD | 5.13E-05 | 5.13E-05 | 5.23E-05 | 1.75E-04 | 0.1029993 | 2.60E-05 | 1.98E-03 | 4.73E-04 | 4.12E-05 | 1.00E-30 | 8.57E-14 | 0 | 0 |
| METHANOL | 0.4340015 | 0.4339993 | 0.4335896 | 0.4117019 | 0.44011 | 0.5464097 | 0.2826034 | 0.01694 | 0.0175065 | 0.3996802 | 1.13E-04 | 7.48E-04 | 0.7986125 |
| CH4O2 | 0.0390817 | 0.0390792 | 0.0388358 | 0.0250754 | 7.35E-04 | 1.12E-04 | 4.12E-06 | 8.55E-03 | 9.62E-03 | 1.00E-30 | 1.93E-23 | 0 | 0 |
| C2H6O3 | 8.04E-03 | 8.04E-03 | 7.96E-03 | 3.98E-03 | 1.88E-18 | 4.49E-07 | 1.44E-21 | 2.68E-04 | 2.41E-04 | 0 | 0 | 0 | 0 |
| C3H8O4 | 7.28E-04 | 7.28E-04 | 7.20E-04 | 3.20E-04 | 8.61E-20 | 1.13E-09 | 3.00E-24 | 8.04E-06 | 5.67E-06 | 0 | 0 | 0 | 0 |
| C4H10O5 | 6.58E-05 | 6.58E-05 | 6.50E-05 | 2.57E-05 | 4.05E-21 | 2.86E-12 | 6.44E-27 | 2.40E-07 | 1.33E-07 | 0 | 0 | 0 | 0 |
| C5H12O6 | 5.95E-06 | 5.95E-06 | 5.87E-06 | 2.06E-06 | 1.92E-22 | 7.19E-15 | 1.40E-29 | 7.16E-09 | 3.12E-09 | 1.00E-30 | 1.29E-09 | 0 | 0 |
| C2H6O2 | 0.0760462 | 0.0760485 | 0.0764416 | 0.0971938 | 0.0185835 | 4.93E-03 | 6.16E-04 | 1.78E-03 | 1.23E-03 | 0 | 0 | 0 | 0 |
| C3H8O3 | 1.25E-03 | 1.25E-03 | 1.27E-03 | 2.29E-03 | 1.90E-18 | 4.71E-06 | 1.32E-20 | 2.00E-05 | 8.82E-06 | 0 | 0 | 0 | 0 |
| C4H10O4 | 3.46E-05 | 3.46E-05 | 3.53E-05 | 8.99E-05 | 4.93E-20 | 7.52E-09 | 2.19E-23 | 3.75E-07 | 1.06E-07 | 0 | 0 | 0 | 0 |
| C5H12O5 | 9.49E-07 | 9.49E-07 | 9.75E-07 | 3.51E-06 | 1.21E-21 | 1.19E-11 | 3.45E-26 | 7.01E-09 | 1.26E-09 | 0 | 0 | 0 | 0 |
| C6H14O6 | 2.60E-08 | 2.60E-08 | 2.69E-08 | 1.37E-07 | 2.96E-23 | 1.89E-14 | 5.23E-29 | 1.31E-10 | 1.49E-11 | 0 | 0 | 0 | 0 |
| ME-ACETA | 0 | 0 | 0 | 0 | 0 | 0 | 0 | 0 | 0 | 0 | 0 | 0 | 0 |
| ME-FORMA | 0 | 0 | 0 | 0 | 0 | 0 | 0 | 0 | 0 | 0 | 0 | 0 | 0 |
| METHYLAL | 0 | 0 | 0 | 0 | 0 | 0.2829908 | 0.6298175 | 2.92E-03 | 2.92E-03 | 0.5670226 | 3.14E-03 | 0.999252 | 0.1347932 |
| POLDME-2 | 0 | 0 | 0 | 0 | 0 | 1.19E-04 | 6.09E-05 | 1.76E-05 | 1.76E-05 | 1.00E-30 | 6.47E-03 | 0 | 0 |
| POLDME-3 | 0 | 0 | 0 | 0 | 0 | 0 | 0 | 0 | 0 | 1.00E-30 | 0.9766289 | 0 | 0 |
| POLDME-4 | 0 | 0 | 0 | 0 | 0 | 0 | 0 | 0 | 0 | 0 | 0 | 0 | 0 |

Fig. 4

Table 2.

| Mass Flow lb/hr | 100 | 101 | 102 | 103 | 104 | 201 | 202 | 301 | 302 | 401 | 501 | 601 | 701 |
|---|---|---|---|---|---|---|---|---|---|---|---|---|---|
| ETHANOL | 51.93744 | 51.93744 | 51.93744 | 51.93744 | 51.93744 | 43.22041 | 43.22041 | 8.717023 | 8.717023 | 42.7146 | 0.5058095 | 1.86E-07 | 42.7146 |
| H2O | 242.2489 | 242.2503 | 242.4471 | 253.2788 | 270.3131 | 26.98527 | 27.01292 | 316.9556 | 316.6133 | 5.02E-28 | 2.36E-12 | 0 | 0 |
| FORMALD | 0.0509229 | 0.050923 | 0.0518966 | 0.1734408 | 114.0187 | 0.0115078 | 1.710656 | 0.2607222 | 0.0227173 | 8.36E-28 | 2.07E-12 | 0 | 0 |
| METHANOL | 459.905 | 459.9025 | 459.4689 | 436.3281 | 519.9038 | 257.8533 | 259.9486 | 9.961036 | 10.28968 | 356.6108 | 2.91E-03 | 0.3336869 | 356.2771 |
| CH4O2 | 62.09151 | 62.08754 | 61.70085 | 39.84374 | 1.302444 | 0.0790915 | 5.68E-03 | 7.535383 | 8.474963 | 1.34E-27 | 7.47E-22 | 0 | 0 |
| C2H6O3 | 20.76356 | 20.76381 | 20.56201 | 10.28574 | 5.41E-15 | 5.16E-04 | 3.22E-18 | 0.3844316 | 0.3445743 | 0 | 0 | 0 | 0 |
| C3H8O4 | 2.603063 | 2.603072 | 2.574759 | 1.145822 | 3.43E-16 | 1.81E-06 | 9.30E-21 | 0.0159478 | 0.0112326 | 0 | 0 | 0 | 0 |
| C4H10O5 | 0.3006498 | 0.3006482 | 0.2970262 | 0.1174931 | 2.06E-17 | 5.81E-09 | 2.55E-23 | 6.08E-04 | 3.37E-04 | 0 | 0 | 0 | 0 |
| C5H12O6 | 0.0330918 | 0.0330914 | 0.0326539 | 0.011479 | 1.19E-18 | 1.78E-11 | 6.76E-26 | 2.21E-05 | 9.63E-06 | 0 | 6.42E-08 | 0 | 0 |
| C2H6O2 | 156.0766 | 156.0812 | 156.8882 | 199.5043 | 42.51803 | 4.505009 | 1.09745 | 2.025726 | 1.402236 | 1.73E-27 | 0 | 0 | 0 |
| C3H8O3 | 3.8193 | 3.81938 | 3.866195 | 6.960476 | 6.44E-15 | 6.38E-03 | 3.50E-17 | 0.0337519 | 0.0148926 | 0 | 0 | 0 | 0 |
| C4H10O4 | 0.1398165 | 0.1398182 | 0.1425292 | 0.3632205 | 2.22E-16 | 1.35E-05 | 7.67E-20 | 8.42E-04 | 2.37E-04 | 0 | 0 | 0 | 0 |
| C5H12O5 | 4.78E-03 | 4.78E-03 | 4.90E-03 | 0.0176823 | 6.81E-18 | 2.68E-08 | 1.51E-22 | 1.96E-05 | 3.51E-06 | 0 | 0 | 0 | 0 |
| C6H14O6 | 1.57E-04 | 1.57E-04 | 1.62E-04 | 8.26E-04 | 1.99E-19 | 5.08E-11 | 2.74E-25 | 4.37E-07 | 4.99E-08 | 0 | 0 | 0 | 0 |
| ME-ACETA | 0 | | | 0 | 0 | 0 | 0 | 0 | 0 | 0 | 0 | 0 | 0 |
| ME-FORMA | 0 | | | 0 | 0 | 0 | 0 | 0 | 0 | 0 | 0 | 0 | 0 |
| METHYLAL | 0 | 0 | 0 | 0 | 0 | 317.1486 | 1375.818 | 4.077531 | 4.077531 | 1201.485 | 0.1921015 | 1058.669 | 142.8091 |
| POLDME-2 | 0 | 0 | 0 | 0 | 0 | 0.1856764 | 0.1856764 | 0.0343355 | 0.0343355 | 2.96E-27 | 0.551957 | 0 | 0 |
| POLDME-3 | 0 | 0 | 0 | 0 | 0 | 0 | 0 | 0 | 0 | 3.79E-27 | 106.9364 | 0 | 0 |
| POLDME-4 | 0 | 0 | 0 | 0 | 0 | 0 | 0 | 0 | 0 | 0 | 0 | 0 | 0 |

Fig. 5

Table 3.

| Mass Fraction | 100 | 101 | 102 | 103 | 104 | 201 | 202 | 301 | 302 | 401 | 501 | 601 | 701 |
|---|---|---|---|---|---|---|---|---|---|---|---|---|---|
| ETHANOL | 0.0519374 | 0.0519387 | 0.0519387 | 0.051939 | 0.0519377 | 0.0664933 | 0.0252898 | 0.0249055 | 0.0249055 | 0.0266831 | 4.68E-03 | 1.76E-10 | 0.0788382 |
| H2O | 0.2422489 | 0.2422564 | 0.2424532 | 0.2532868 | 0.2703149 | 0.041516 | 0.0158062 | 0.9055797 | 0.9046015 | 3.13E-31 | 2.18E-14 | 0 | 0 |
| FORMALD | 5.09E-05 | 5.09E-05 | 5.19E-05 | 1.73E-04 | 0.1140194 | 1.77E-05 | 1.00E-03 | 7.45E-04 | 6.49E-05 | 5.22E-31 | 1.91E-14 | 0 | 0 |
| METHANOL | 0.459905 | 0.4599142 | 0.4594805 | 0.4363418 | 0.5199072 | 0.3967 | 0.1521057 | 0.0284598 | 0.0293988 | 0.2227689 | 2.69E-05 | 3.15E-04 | 0.6575795 |
| CH4O2 | 0.0620915 | 0.0620891 | 0.0617024 | 0.0398449 | 1.30E-03 | 1.22E-04 | 3.33E-06 | 0.0215294 | 0.0242139 | 8.36E-31 | 6.90E-24 | 0 | 0 |
| C2H6O3 | 0.0207635 | 0.0207643 | 0.0205625 | 0.010286 | 5.41E-18 | 7.94E-07 | 1.89E-21 | 1.10E-03 | 9.84E-04 | 0 | 0 | 0 | 0 |
| C3H8O4 | 2.60E-03 | 2.60E-03 | 2.57E-03 | 1.15E-03 | 3.43E-19 | 2.78E-09 | 5.44E-24 | 4.56E-05 | 3.21E-05 | 0 | 0 | 0 | 0 |
| C4H10O5 | 3.01E-04 | 3.01E-04 | 2.97E-04 | 1.17E-04 | 2.06E-20 | 8.94E-12 | 1.49E-26 | 1.74E-06 | 9.63E-07 | 0 | 0 | 0 | 0 |
| C5H12O6 | 3.31E-05 | 3.31E-05 | 3.27E-05 | 1.15E-05 | 1.19E-21 | 2.74E-14 | 3.96E-29 | 6.32E-08 | 2.75E-08 | 0 | 0 | 0 | 0 |
| C2H6O2 | 0.1560766 | 0.1560852 | 0.1568922 | 0.1995105 | 0.0425183 | 6.93E-03 | 6.42E-04 | 5.79E-03 | 4.01E-03 | 1.08E-30 | 5.94E-10 | 0 | 0 |
| C3H8O3 | 3.82E-03 | 3.82E-03 | 3.87E-03 | 6.96E-03 | 6.44E-18 | 9.82E-06 | 2.05E-20 | 9.64E-05 | 4.26E-05 | 0 | 0 | 0 | 0 |
| C4H10O4 | 1.40E-04 | 1.40E-04 | 1.43E-04 | 3.63E-04 | 2.22E-19 | 2.08E-08 | 4.49E-23 | 2.40E-06 | 6.76E-07 | 0 | 0 | 0 | 0 |
| C5H12O5 | 4.78E-06 | 4.78E-06 | 4.90E-06 | 1.77E-05 | 6.81E-21 | 4.12E-11 | 8.82E-26 | 5.59E-08 | 1.00E-08 | 0 | 0 | 0 | 0 |
| C6H14O6 | 1.57E-07 | 1.57E-07 | 1.62E-07 | 8.26E-07 | 1.99E-22 | 7.81E-14 | 1.60E-28 | 1.25E-09 | 1.42E-10 | 0 | 0 | 0 | 0 |
| ME-ACETA | 0 | 0 | 0 | 0 | 0 | 0 | 0 | 0 | 0 | 0 | 0 | 0 | 0 |
| ME-FORMA | 0 | 0 | 0 | 0 | 0 | 0 | 0 | 0 | 0 | 0 | 0 | 0 | 0 |
| METHYLAL | 0 | 0 | 0 | 0 | 0 | 0.4879241 | 0.805043 | 0.0116499 | 0.0116499 | 0.750548 | 1.78E-03 | 0.9996849 | 0.2635823 |
| POLDME-2 | 0 | 0 | 0 | 0 | 0 | 2.86E-04 | 1.09E-04 | 9.81E-05 | 9.81E-05 | 1.85E-30 | 5.10E-03 | 0 | 0 |
| POLDME-3 | 0 | 0 | 0 | 0 | 0 | 0 | 0 | 0 | 0 | 2.37E-30 | 0.9884205 | 0 | 0 |
| POLDME-4 | 0 | 0 | 0 | 0 | 0 | 0 | 0 | 0 | 0 | 0 | 0 | 0 | 0 |

Fig. 6

Table 4.

| | 100 | 101 | 102 | 103 | 104 | 201 | 202 | 301 | 302 | 401 | 501 | 601 | 701 |
|---|---|---|---|---|---|---|---|---|---|---|---|---|---|
| Total Flow lbmol/hr | 33.07159 | 33.07159 | 33.07162 | 33.07567 | 36.86719 | 14.72762 | 28.70703 | 18.35134 | 18.34341 | 27.84582 | 0.804239 | 13.92283 | 13.92291 |
| Total Flow lb/hr | 1000 | 999.9747 | 999.9747 | 999.9686 | 999.9935 | 649.9958 | 1708.999 | 350.003 | 350.0031 | 1600.81 | 108.1892 | 1059.003 | 541.8008 |
| Total Flow cuft/hr | 17.81496 | 17.81495 | 17.81961 | 18.22397 | 11892.78 | 13.68805 | 12285.54 | 6.296713 | 5.892457 | 32.12392 | 0.3044073 | 4879.519 | 11.54194 |
| Temperature F | 80 | 80 | 80.55747 | 121.701 | 300 | 171.3337 | 230 | 230.4313 | 126.7039 | 126.1301 | 442.5029 | 115.822 | 153.081 |
| Pressure psia | 15 | 15 | 70 | 70 | 25 | 25 | 17 | 26 | 62 | 20 | 20 | 17 | 17 |
| Vapor Frac | 0 | 0 | 0 | 0 | 1 | 0 | 1 | 0 | 0 | 0 | 0 | 1 | 0 |
| Liquid Frac | 1 | 1 | 1 | 1 | 0 | 1 | 0 | 1 | 1 | 1 | 1 | 0 | 1 |
| Solid Frac | 0 | 0 | 0 | 0 | 0 | 0 | 0 | 0 | 0 | 0 | 0 | 0 | 0 |
| Enthalpy Btu/lbmol | -1.23E+05 | -1.23E+05 | -1.23E+05 | -1.22E+05 | -89478.75 | -1.21E+05 | -1.25E+05 | -1.21E+05 | -1.23E+05 | -1.35E+05 | -3.66E+05 | -1.49E+05 | -1.10E+05 |
| Enthalpy Btu/lb | -4064.78 | -4064.882 | -4064.268 | -4027.895 | -3298.851 | -2731.264 | -2095.846 | -6320.062 | -6424.051 | -2354.916 | -2723.037 | -1957.448 | -2823.565 |
| Enthalpy Btu/hr | -4.06E+06 | -4.06E+06 | -4.06E+06 | -4.03E+06 | -3.30E+06 | -1.78E+06 | -3.58E+06 | -2.21E+06 | -2.25E+06 | -3.77E+06 | -2.95E+05 | -2.07E+06 | -1.53E+06 |
| Entropy Btu/lbmol-R | -54.33645 | -54.33632 | -54.29037 | -51.19703 | -16.34701 | -68.42007 | -66.23787 | -35.59681 | -38.73861 | -89.71354 | -208.8921 | -96.43142 | -62.93232 |
| Entropy Btu/lb-R | -1.796993 | -1.797034 | -1.795516 | -1.693429 | -0.6026722 | -1.550263 | -1.112635 | -1.86641 | -2.030263 | -1.560552 | -1.552828 | -1.267794 | -1.617202 |
| Density lbmol/cuft | 1.856394 | 1.856395 | 1.855911 | 1.814954 | 3.10E-03 | 1.075947 | 2.34E-03 | 2.914432 | 3.113033 | 0.8668252 | 2.641984 | 2.855E-03 | 1.206289 |
| Density lb/cuft | 56.13259 | 56.13121 | 56.11653 | 54.87107 | 0.0840841 | 47.48635 | 0.1391066 | 55.58503 | 59.39849 | 49.83235 | 355.4094 | 0.2170302 | 46.94192 |
| Average MW | 30.23744 | 30.23667 | 30.23664 | 30.22276 | 27.12421 | 44.13448 | 59.53243 | 19.07234 | 19.08059 | 57.48835 | 134.5237 | 76.06237 | 38.91434 |
| Liq Vol 60F cuft/hr | 17.92294 | 17.92291 | 17.91968 | 17.73777 | 18.89509 | 12.52655 | 32.41673 | 5.72116 | 5.725146 | 30.59671 | 1.602796 | 19.86928 | 10.72731 |
| *** ALL PHASES *** | | | | | | | | | | | | | |
| Temperature F | 80 | | | | 300 | 171.3337 | 230 | 230.4313 | 126.7039 | 126.1301 | 442.5029 | 115.822 | 153.081 |
| *** VAPOR PHASE *** | | | | | | | | | | | | | |
| MUMX lb/ft-hr | | | | | 0.0351747 | | 0.0276147 | | | | | 0.021596 | |
| MASSRHOM lb/cuft | | | | | 0.0840841 | | 0.1391066 | | | | | 0.2170302 | |
| KMX Btu/hr-ft-F | | | | | 0.0164133 | | 0.0125253 | | | | | 8.53E-03 | |
| Average MW | | | | | 27.12421 | | 59.53243 | | | | | 76.06237 | |
| Enthalpy Btu/lb | | | | | -3298.851 | | -2095.846 | | | | | -1957.448 | |
| *** LIQUID_1 PHASE * | | | | | | | | | | | | | |

Fig. 7

UPGRADING OF A RAW BLEND INTO A DIESEL FUEL SUBSTITUTE: POLY(DIMETHOXYMETHANE)

CROSS-REFERENCE TO RELATED APPLICATIONS

This application is a division U.S. application Ser. No. 16/434,318 filed Jun. 7, 2019, now U.S. Pat. No. 11,103,849 issued Aug. 31, 2021, which is a division of U.S. application Ser. No. 15/693,991 filed Sep. 1, 2017, now U.S. Pat. No. 10,322,397 issued Jun. 18, 2019, the disclosures of which are hereby incorporated in their entirety by reference herein.

TECHNICAL FIELD

In at least one aspect, the present invention is related to a method and systems for producing poly(dimethoxymethane) from a raw blend that includes formaldehyde and methanol.

BACKGROUND

Polyoxymethylene dimethyl ethers, also referred to as Poly(dimethoxymethane), can be synthesized to present properties compatible with those of conventional diesel fuel. It has the chemical structure of $CH_3$—O—$(CH_2$—O$)_n$—$CH_3$. Poly(dimethoxymethane) with n=1 is dimethoxymethane (DMM), which although it has attractive properties for fuels applications, when n ranges from 3 to 5 the poly(dimethoxymethane) can be blended directly into diesel with no need for engine modifications. Furthermore, because there are no carbon-carbon bonds in the poly(dimethoxymethane) molecule, the fuel burns clean without the generation of soot.

Poly(dimethoxymethane) can be synthesized from methanol and formaldehyde as depicted from the following equation:

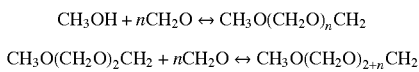

$$CH_3OH + nCH_2O \leftrightarrow CH_3O(CH_2O)_nCH_2$$

$$CH_3O(CH_2O)_2CH_2 + nCH_2O \leftrightarrow CH_3O(CH_2O)_{2+n}CH_2$$

For initial dimethoxymethane synthesis or further production of poly(dimethoxymethane), it is necessary to understand the dynamics of formaldehyde in solution. Formaldehyde readily reacts with water and methanol to produce methylene glycol ($HOCH_2OH$, MG), poly(oxymethylene) glycols ($H(OCH_2)_nOH$, $MG_n$, n>1), hemiformal ($HOCH_2OCH_3$, HF), and poly(oxymethylene) hemiformals ($H(OCH_2)_nOCH_3$, $HF_n$, n>1). The model presented for poly(dimethoxymethane) production takes into consideration the equilibrium conditions for formaldehyde and its availability for the dimethoxymethane synthesis reaction. Although processes for forming poly(dimethoxymethane) are known, the costs of synthesis can be unreasonably high thereby inhibiting its application in products such as diesel fuel.

Accordingly, there is a need for improved methods and systems for producing poly(dimethoxymethane).

SUMMARY

The present invention solves one or more problems of the prior art by providing in at least one embodiment, a method for forming poly(dimethoxymethane). The method includes a step of separating a formaldehyde-containing blend into a first bottom stream and a first top stream. The first formaldehyde-containing blend includes methanol, formaldehyde, and water while the first bottom stream includes water. The first top stream includes dimethoxymethane that is produced from the reaction between methanol and formaldehyde. The first top stream is separated into a second bottom stream and a second top stream. The second bottom stream includes poly(dimethoxymethane) while the second top stream includes dimethoxymethane, methanol, and ethanol. The second top stream is separated into a third bottom stream and a third top stream. The third bottom stream includes methanol and ethanol while the third top stream includes dimethoxymethane. The third top steam can be recycled to form additional poly(dimethoxymethane).

In another embodiment, a system for forming poly(dimethoxymethane) using the method set forth above is provided. The system includes a first separation station that receives a formaldehyde-containing blend and outputs a first bottom stream and a first top stream. The formaldehyde-containing blend includes methanol, formaldehyde, and water. The first top stream includes dimethoxymethane that is produced from the reaction between methanol and formaldehyde as well as unreacted methanol and formaldehyde, while the bottom stream includes water. A second separation station receives the first top stream and outputs a second bottom stream and a second top stream. The second bottom stream includes poly(dimethoxymethane) while the second top stream including dimethoxymethane, methanol, and ethanol. A third separation station receives the second top stream and outputs a third bottom stream and a third top stream. The third bottom stream includes methanol and ethanol and the third top stream including dimethoxymethane.

In another embodiment, a natural gas liquids plant is provided. The natural gas liquids plant includes a natural gas compressor that receives that receives and compresses natural gas to a pressure of 850 to 1100 psig. The natural gas compressor includes a cooler that cools the natural gas after compression to provide a compressed rich gas stream containing 5% or more C3-8 hydrocarbons. A methanol source from which methanol is injected into the compressed rich gas stream. A plurality of heat transfer units to cool the compressed rich gas stream to a sufficient temperature for separation of propane and higher hydrocarbons. The plurality of heat transfer units includes a first heat exchanger that to initially cool the rich gas stream to a first cooled stream, a second heat exchanger that cools the first cooled stream to a second cooled stream, and a third heat exchanger that cools the second cooled stream to a third cooled gas stream. The natural gas liquids plant also includes a vapor-liquid-liquid separator, a vapor-liquid separator, and an NGL stabilization column. The vapor-liquid-liquid separator separates the third cooled gas stream into a first three-phase separated vapor stream and a first three-phase separated liquid stream including water and methanol and a second three-phase separated liquid stream including natural gas liquids. The vapor-liquid separator separates the first three-phase separated vapor stream into a second two-phase separated vapor stream and a second two-phase separated liquid stream. The stabilization column separates the second two-phase separated liquid stream into a stabilization column separated vapor stream and a stabilization column separated liquid stream. Characteristically, the stabilization column separated liquid stream includes greater than 50% C3+ hydrocarbons.

BRIEF DESCRIPTION OF THE DRAWINGS

FIG. 4 provides Table 1 showing values of the mole fraction at specified regions of the system of FIG. 1.

FIG. 5 provides Table 2 showing values of the mass flow at specified regions of the system of FIG. 2.

FIG. 6 provides Table 3 showing values of the mass fraction at specified regions of the system of FIG. 2.

FIG. 7 provides Table 4 showing values of various properties at specified regions of the system of FIG. 2.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As used herein "poly(dimethoxymethane)" without a subscript refers polyoxymethylene dimethyl ethers which can be formed from methanol and formaldehyde. In a variation, poly(dimethoxymethane) has the following formula:

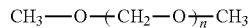

where n is 2 to 8 (i.e., 2, 3, 4, 5, 6, 7, 8). This formula can also be expressed as poly(dimethoxymethane)$_n$. In a refinement, n is 3 to 8. In still another refinement, n is 3 to 5.

As used herein "top stream" means the relatively volatile components compared to the "bottom stream" that are removed in a separation station.

As used herein "bottom stream" means the less volatile components compared to the "top stream" that are removed in a separation station. In a separation column, the top stream exits at the top of the column while the bottom stream exits at the bottom of the column.

Figure 1:
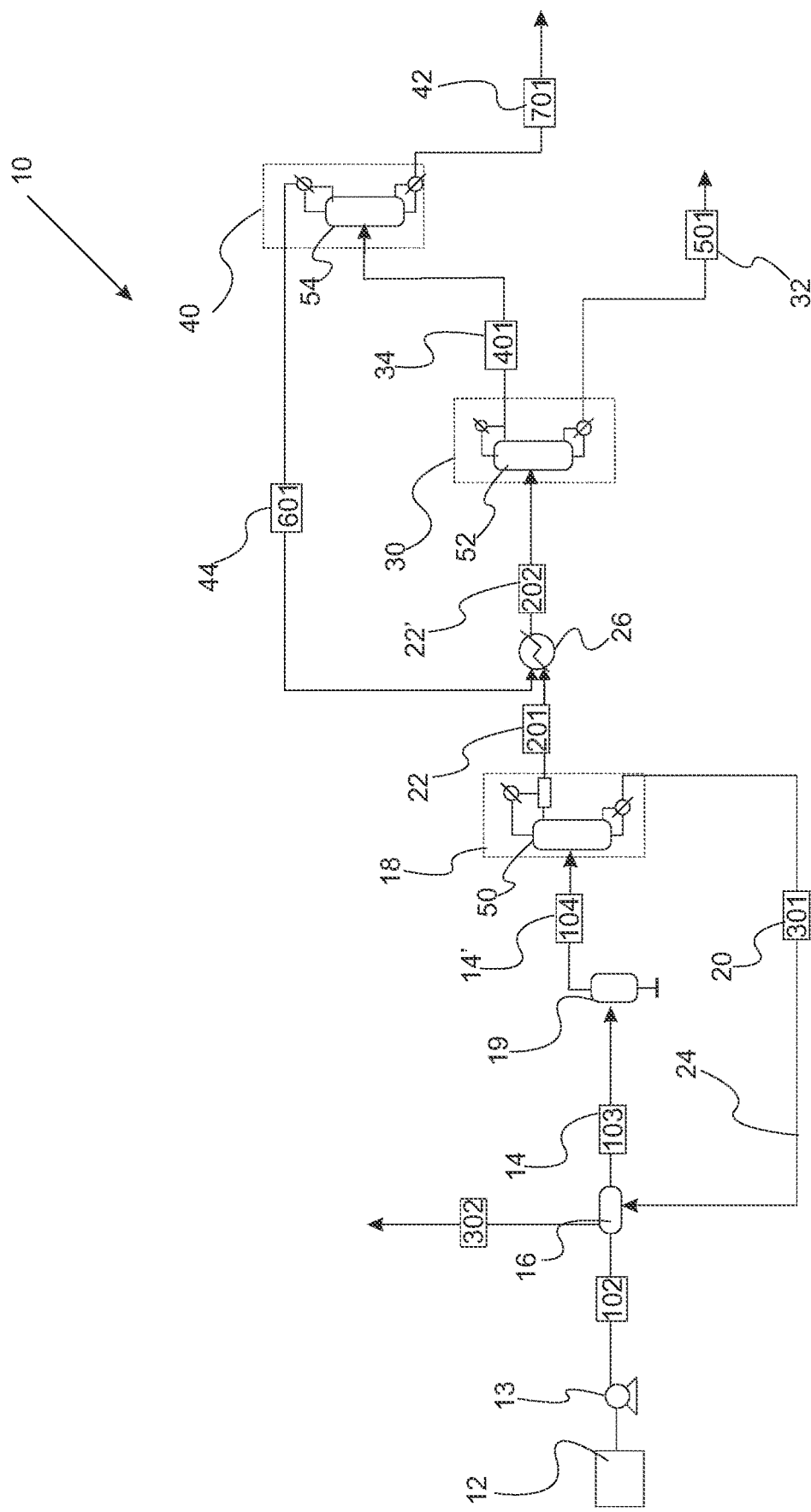
FIG. 1 is a schematic illustration of a system for forming poly(dimethoxymethane).

With reference to FIG. 1, a schematic illustration of a system for forming poly(dimethoxymethane) is provided. System 10 includes source 12 of a formaldehyde-containing blend 14 that is provided to a first separation station 18 via pump 13. Heat exchanger 16 can optionally be used to recover heat from the first bottom stream 20 to heat the formaldehyde-containing blend 14. In a refinement, heater 19 is used to heat formaldehyde-containing blend 14 to form heated formaldehyde-containing blend 14'. The heated formaldehyde-containing blend is found at a temperature near the boiling point of the stream, in the range of 250 to 275 F. The high temperatures facilitate breakdown of poly(oxymethylene) glycols and poly(oxymethylene) hemiformals into the simple components of formaldehyde, methanol, water and shorter oligomers. First separation station 18 outputs first bottom stream 20 and first top stream 22. Formaldehyde-containing blend 14 includes methanol, formaldehyde, and water. First bottom stream 20 includes water (e.g. 30-100 mole percent). First top stream 22 includes dimethoxymethane that is produced from the reaction between methanol and formaldehyde. In a refinement, first separation station 18 is performed by reactive distillation. Details for reactive distillation are set forth in U.S. Pat. Pub. No. 20170081602; the entire disclosure of which is hereby incorporated by reference. In general, reactive distillation uses a catalyst-packed column having a catalyst that converts alcohols to ethers and/or ketones and aldehydes. When reactive distillation is deployed, operating pressures are typically between 0 and 250 psia, preferably between 14.7 and 150 psi. In a refinement, the catalyst is an immobilized catalyst. Examples of such catalysts include, but are not limited to, aluminosilicate catalysts, copper modified alumina catalyst, combinations thereof and the like. At these elevated pressures the boiling point of methanol is increased to the preferred temperatures for alcohol dehydration, between 50 and 300° C., and preferably between 150 and 250° C.

In a refinement, the heat from the first bottom stream can be transferred to the formaldehyde-containing stream 14. In a refinement, heater 26 can be used to heat first top stream 22 to form heated top stream 22'. First top stream 22' is introduced into second separation station 30 that outputs second bottom stream 32 and a second top stream 34. Second bottom stream 32 includes poly(dimethoxymethane) while second top stream 34 including dimethoxymethane. Second top stream 34 is introduced into a third separation station 40 that outputs a third bottom stream 42 and third top stream 44. Third bottom stream 42 includes methanol and ethanol while the third top stream 44 includes dimethoxymethane.

In a variation, formaldehyde-containing blend 14 includes up to 40 mole % water. In a refinement, formaldehyde-containing blend 14 includes from 5 to 30 mole % water. Moreover, the first feed stream can also include methylal, methanol, ethanol, formaldehyde and its derivatives in solution, as well as minor concentrations of higher alcohols (e.g. propanol) and weak acids (e.g. formic acid, acetic acid).

In another variation, the first separation station 18 includes and/or is a first separation column 50. In a refinement, the first separation column including an acid catalyst that promotes acetylation. Examples of such catalysts include, but are not limited to, aluminosilicate catalysts, copper modified alumina catalyst, sulfonic acid ion exchange resins, ionic liquids and combinations thereof and the like. Operating temperatures and pressures range from 15-30 psig and 170-250° F.

In a variation, second separation station 30 includes and/or is a second separation column 52. In a refinement, second separation station 30 includes an acid catalyst that accelerates equilibrium between DMM-formaldehyde-methanol. Examples of such catalysts include, but are not limited to, aluminosilicate catalysts, copper modified alumina catalysts, sulfonic acid ion exchange resins, ionic liquids and combinations thereof and the like. In a further refinement, the acid catalyst also promotes reaction between dimethoxymethane, poly(dimethoxymethane), and formaldehyde to produce

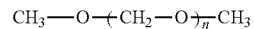

with n=3-5. Acquisition of poly(DMM) in the desired boiling range, e.g. n=3-5, is controlled by the column temperature. Furthermore, the presence of water tends to reduce selectivity to poly(DMM) in the n=3-5 range and increase selectivity of poly(DMM)$_2$, therefore by removing nearly all water in the first separation station the present process maximizes synthesis of poly(DMM)$_{3-5}$. Unreacted light components such as DMM and poly(DMM)$_2$ can be recycled for their upgrade to poly(DMM)$_{3-5}$. In a further refinement, second separation station 30 includes a catalytic reaction vessel followed by a distillation column. The same catalyst can be used for both the synthesis of DMM as well as Poly(DMM), therefore the catalysts of potential application in separation 30 include, but are not limited to, aluminosilicate catalysts, copper modified alumina catalysts, sulfonic acid ion exchange resins, ionic liquids and combinations thereof and the like.

In another variation, the second separation station 30 includes a reactor vessel containing an acid catalyst that accelerates equilibrium between DMM-formaldehyde-methanol, and also promotes reaction between dimethoxymethane, poly(dimethoxymethane), and formaldehyde to produce Poly(DMM)$_{3-5}$. The same catalyst can be used for both the synthesis of DMM as well as Poly(DMM), therefore the catalysts of potential application in separation 30 include, but are not limited to, aluminosilicate catalysts, copper modified alumina catalysts, sulfonic acid ion exchange resins, ionic liquids and combinations thereof and the like. Both variations of separation station 30 operate at low pressure (5-25 psig) and temperatures in the range of 125 to 300° F.

In a variation, the third separation station 40 is a distillation column 54 in which dimethoxymethane is separated from the alcohols methanol and ethanol. This separation station operates at near ambient pressure (5-10 psig) and temperatures ranging from 110 to 175° F.

Figure 2:
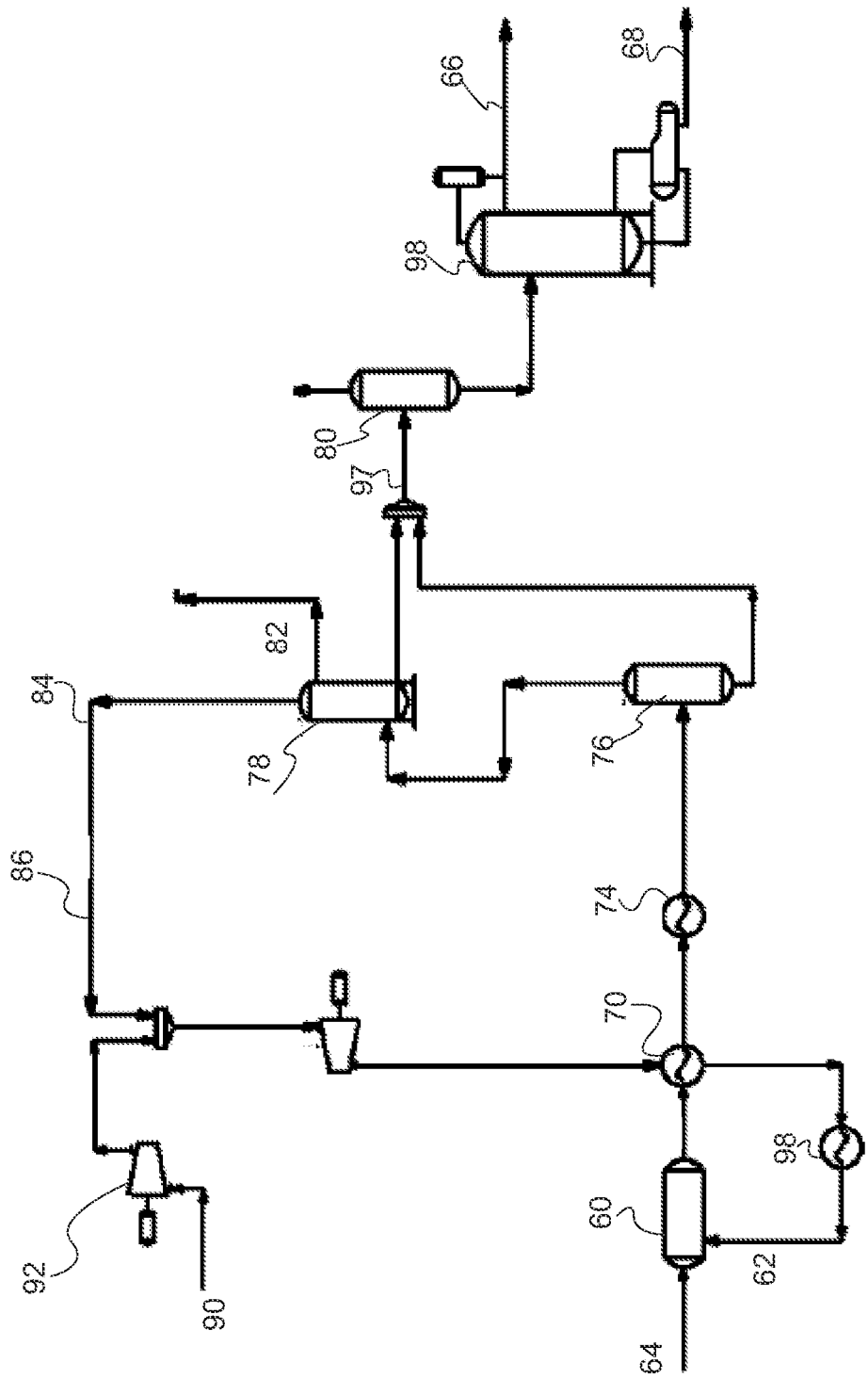
FIG. 2 is a schematic illustration of a system for forming gas-to-liquids (GTL).

The system of FIG. 1 can use many types of blends of hydrocarbon liquids with partial oxygenates thereof as a feedstock. In some variations, the feedstock is the product of a gas-to-liquids process which is understood to include processes that converts methane and/or blends of $C_{1-4}$ alkanes into longer hydrocarbon chains (e.g., $C_{5-10}$ alkanes) with partial oxygenates of $C_{1-4}$ alkanes (formaldehyde, aldehydes, ketones, alcohols, and the like). With reference to FIG. 2, a schematic illustration of a gas-to-liquids (GTL) system of U.S. Pat. No. 9,255,051 that can be provide the gas blend introduced into the system of FIG. 1. The entire disclosure of U.S. Pat. No. 9,255,051 that is hereby incorporated by reference in its entirety. Homogeneous direct partial oxidation is performed in a reactor 60 which is supplied with a hydrocarbon-containing gas 62 and an oxygen-containing gas 64. Ina refinement, the reaction is operated at pressures from about 450 to 1230 psia and temperatures from about 350 to 450° C. In particular, hydrocarbon-containing gas 62 and an oxygen-containing gas 64 react in a vessel to form a first product blend which is a blend (i.e., a mixture) of partially oxygenated compounds that include formaldehyde. In a refinement, the first product blend and/or output streams 66, 68 include $C_{1-10}$ alcohols and/or $C_{1-5}$ aldehydes. In another refinement, the first product blend and/or output streams 66, 68 include an alcohol selected from the group consisting of methanol, ethanol, propanols (n-propyl alcohol, isopranol), butanols (n-butanol, sec-butanol, t-butanol, isobutanol), pentanols (n-pentanol, isopentanol, sec-pentanol, etc) and combinations thereof, and/or aldehyde selected from the group consisting formaldehyde, acetaldehyde, propionaldehyde and combinations thereof. In another refinement, the first product blend and/or output streams 66, 68 include an alcohol selected from the group consisting of methanol, ethanol, and combinations thereof, and aldehyde selected from the group consisting formaldehyde, acetaldehyde, and combinations thereof. Examples of systems and methods of performing the partial oxidation as set forth in U.S. Pat. Nos. 8,293,186; 8,202,916; 8,193,254; 7,910,787; 7,687,669; 7,642,293; 7,879,296; 7,456,327; and 7,578,981; the entire disclosures of which are hereby incorporated by reference. In a refinement, the hydrocarbon-containing gas includes $C_{1-10}$ alkanes. In another refinement, the hydrocarbon-containing gas includes an alkane selected from the group consisting of methane, ethane, propanes, butanes, pentanes and combinations thereof. In another refinement, the hydrocarbon-containing gas includes an alkane selected from the group consisting of methane, ethane, and combinations thereof. Examples of oxygen containing gas include molecular oxygen which may be in the form of concentrated oxygen or air. In a refinement, the oxygen-containing gas stream is made oxygen rich (e.g., by passing air through a membrane to increase oxygen content). The low conversion and selectivity of homogeneous direct partial oxidation requires that a recycle loop is utilized to increase the overall carbon efficiency.

Following partial oxidation reaction the reactant stream is rapidly cooled in a series of heat exchangers 70 and 74 to prevent decomposition of the produced oxygenates. The heat energy transferred by exchanger 74 might optionally be used to provide energy which may be used in the creation of synthesis gas or to drive downstream distillation processes. After cooling the liquids are separated from the gas stream as station 76. The gas stream is then submitted to a separation process for removal of non-hydrocarbon fractions a station. 78 which may be performed via scrubbing, membrane separation, adsorption processes, cryogenic separations, or by purging a small gas fraction. If station 78 is a liquid scrubbing system, liquid products are sent to a flash drum 80 where dissolved gases are removed. Non-hydrocarbon gases 82 are removed from the recycle loop 84, and the hydrocarbon gases 86 are then recycled to combine with fresh methane gas 90 which has been pressurized to the pressure of the loop by compressor 92. The stream composed of recycled hydrocarbons plus fresh methane gas is pressurized to make up for pressure losses in the recycle loop, preheated via the cross exchanger 70 and further by the preheater 96, when necessary, to meet the desired reaction conditions.

Liquids generated by the gas-to-chemicals process are composed predominantly of alcohols and aldehydes (e.g., methanol, ethanol and formaldehyde) as set forth above. The raw liquid stream 97 generated by the GTL process is generally composed of 40-70 mole % alcohols and 5-20 mote % aldehydes 15-40 mole % water. Downstream processing of these liquids may include a number of different synthesis routes to higher-value chemicals and fuels, but simple distillation of alcohols from aldehydes is performed in a simple fractional distillation column 98 in which alcohols are recovered in the distillate 66 and the aqueous aldehyde solution from the column bottoms 68.

Figure 3:
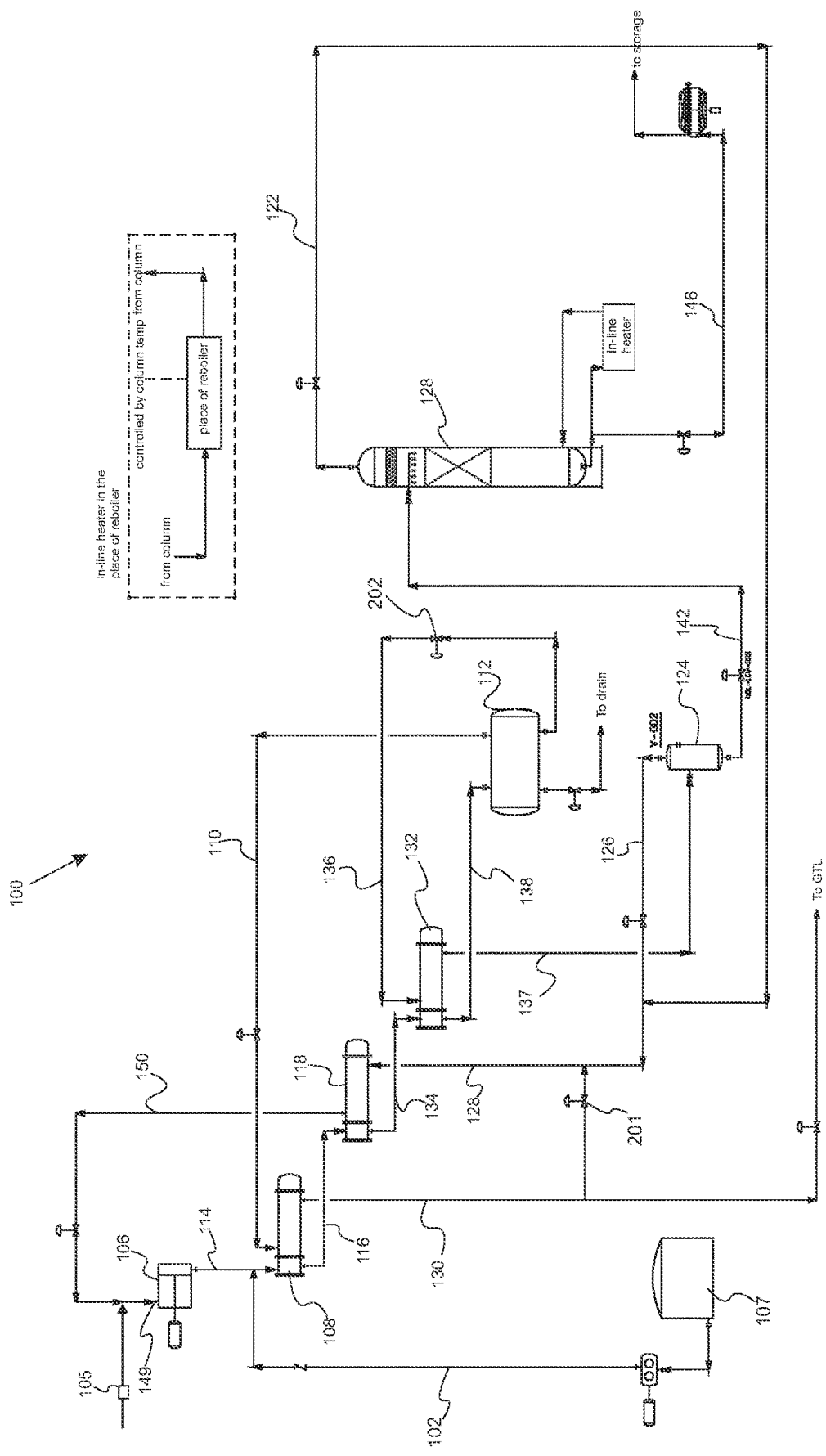
FIG. 3 is a schematic illustration of a high-pressure natural gas liquids (NGL) plant.

FIG. 3 provides a schematic illustration of a high-pressure natural gas liquids (NGL) plant 100 designed with the intent of utilizing the Joules Thompson expansion effect for cooling of rich natural gas for separation of natural gas liquids while also producing a high-pressure lean gas suitable for application in a GTL process. The produced NGL's are dropped from high pressure to the NGL storage pressure and the chilled NGL's are used to remove heat from the incoming raw gas stream, furthermore, an additional portion of the lean gas and that off the top of the stabilization column can be recycled to the compressor suction and also used to remove heat from the incoming raw gas.

With reference to FIG. 3, a Btu-rich natural gas stream containing 5% or more of C3-8 hydrocarbons 105 is first fed to a natural gas compressor 106 where it is compressed to an operating pressure of 850-1100 psig. Following compression, the natural gas flows through the aftercooler of the same compressor 106 so that it reaches a final temperature of approximately ambient+10° F. Methanol from methanol source 107 is then injected into the gas stream 114 at the concentration required to inhibit natural gas hydrate formation. This methanol source may be external or generated by the local gas-to-methanol conversion process.

After this, the gas enters a series of heat transfer units until reaching temperatures adequate for separation of propane and higher hydrocarbons. The first heat exchange unit 108 utilizes the cold lean (from which approximately 80% of C3-8 hydrocarbons have been removed) gas stream 110 exiting the vapor-liquid-liquid separator 112 (i.e., a three phase separator) to initially chill the compressed rich gas 114. Details vapor-liquid separators is found in Cusack R. et al. Hydrocarbon Processing, June 2009, pgs 53-60; the entire disclosure of which is hereby incorporated by reference.

This initially cooled natural gas stream 116 is further cooled in the second heat exchange unit 118 with heat being exchanged via heat transfer to cooling gas 128. The cooling gas 128 is composed of the vapor stream 126 exiting the vapor-liquid separator 124 (i.e., a two-phase separator) and the vapor steam 122 exiting the top of the stabilization column 128. Additionally, in order to meet the overall cooling requirements, a specific portion of the high-pressure lean gas 130 (from which approximately 80% of C3-8 hydrocarbons have been removed) exiting the first heat exchanger unit 108 can be submitted to a pressure drop via a control valve 201 which generates an isenthalpic expansion process also known as Joule-Thomson cooling, and blended into stream 128 to provide additional cooling of the raw rich gas 116 (containing all natural gas liquids as in the initial gas stream 105).

The final heat exchange unit 132 further cools the rich gas 134 (containing all natural gas liquids as in the initial gas stream 105) by transferring heat from the super-cooled NGL liquid stream 136. This unit operation cools the incoming gas to the final separation conditions of approximately 40 F at approximately 1100 psi. This cooled rich gas rich in natural gas liquids (C3-8 hydrocarbons) 138 then enters a vapor-liquid-liquid separator 112 in which the liquids and gas are separated and the two liquids phases (NGL and water/methanol) also separate.

The obtained NGL stream 136 is submitted to a pressure drop, via a control valve 202 which generates an isenthalpic expansion process to approximately 150 psi which results in an extreme cooling effect, making it especially effective to cool the incoming natural gas liquids-rich stream. However, after exiting the final heat exchanger unit 132, some of the light hydrocarbons boil to the vapor phase and therefore need to be separated from the liquids in a simple vapor-liquid separator 124. In this regard, vapor phase stream 137 is provided to the vapor-liquid separator 124. Exiting the vapor-liquid separator 124 is a relatively rich gas stream with high propane concentration (e.g. approximately 1400 btu/scf) 126 and a stable liquid NGL stream 142.

A final separation column, e.g. NGL stabilization column, 128 is utilized to reduce ethane concentrations in the NGL stream while retaining the maximum concentration of C3-8 hydrocarbons. The stabilized liquid stream 146 can optionally be further cooled to ensure its stable storage.

The vapor stream 122 exiting the top of the separation column can also contain up to 20% C3-C8 hydrocarbons and is combined with the vapor stream exiting the vapor-liquid separator 126 to be recycled to the suction side 149 of the compressor 106 as vapor stream 150. Because stream 150 contains a significant amount of propane, by recycling this steam the overall propane recover can be greatly improved, increasing overall propane recovery values to greater than 75%.

The NGL separation column 128 requires a heat source to act as a reboiler for separating the light components (ethane) from the heavy components (propane). This can be accomplished by using a simple electric heater, or via heat integration, where the heat generated by the compressor or the GTL system can be utilized to provide heat to the reboiler.

FIGS. 4-7 provides tables giving values of reaction parameters at position labeled in FIG. 1 used in a thermo-kinetic model of the reactor. The process model was devoted considering the formaldehyde-water-methanol equilibrium data published by Maurer (1980 and component properties derived from the UNIFAC method. Synthesis of poly (DMM) was based on equilibrium conditions based on Gibbs free energy. Table 1 provides the mole fraction for each stream in the system of FIG. 1. First bottom stream 20 includes composition 301 while first top stream 22 includes composition 201 and heat first top stream 22' includes composition 202. Second bottom stream 32 includes composition 501 while second top stream 34 includes composition 401. Third bottom stream 42 includes composition 701 while third top stream 44 includes composition 601. The composition provided to system 10 includes composition 101, the composition after pump 13 includes composition 102. The composition after pump 19 includes composition 103. The composition between heat 19 and first separation station 18 includes composition 104. The composition recycled from and first separation station 18 to pump 16 includes composition 3M. FIG. 5 provides Table 2 showing values of the mass flow at specified regions of the system of FIG. 1. FIG. 6 provides Table 3 showing values of the mass fraction at specified regions of the system of FIG. 1. FIG. 7 provides Table 4 showing values of various properties at specified regions of the system of FIG. 1. In various embodiments of the systems of FIG. 1, the values in Tables 1-4 can vary within a range of +/−30 percent of the indicated value with the understanding that percentages will be truncated at 0 or 100 percent when applicable and fractions will be truncated at 0 and 1 when applicable.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for forming poly(dimethoxymethane) comprising:
   a source that provides a feedstock, the feedstock includes a first formaldehyde-containing blend;
   a heater configured to heat the first formaldehyde-containing blend to breakdown poly(oxymethylene) glycols and poly(oxymethylene) hemiformals into formaldehyde, methanol, water and shorter oligomers to form a second formaldehyde-containing blend;
   a first reaction and separation station that receives the second formaldehyde-containing blend as the feedstock and outputs a first bottom stream and a first top stream, the first reaction and separation station positioned downstream of the heater, the second formaldehyde-containing blend including methanol, formaldehyde, and water, the first top stream including dimethoxymethane that is produced from a reaction between methanol and formaldehyde, the first bottom stream including water;

a second reaction and separation station that receives the first top stream and outputs a second bottom stream and a second top stream, the second bottom stream including poly(dimethoxymethane) and the second top stream including dimethoxymethane, methanol and ethanol; and a third separation station that receives the second top stream and outputs a third bottom stream and a third top stream, the third bottom stream including methanol and ethanol and the third top stream including dimethoxymethane.

2. The system of claim 1 wherein the feedstock is composed of at least 40-70 mole % alcohols, 5-20 mole % aldehydes and 15-40 mole % water.

3. The system of claim 1 further comprising a recycle loop that recycles dimethoxymethane from the third separation station back to the second reaction and separation station.

4. The system of claim 1 wherein the second formaldehyde-containing blend includes up to 30 mole % water.

5. The system of claim 1 wherein the first top stream includes methylal, methanol, ethanol and unreacted formaldehyde.

6. The system of claim 1 wherein the first reaction and separation station includes a first separation column.

7. The system of claim 6 wherein the first separation column including an acid catalyst that promotes acetylation.

8. The system of claim 1 wherein the second reaction and separation station includes a second separation column.

9. The system of claim 8 wherein the second separation column includes an acid catalyst that promotes equilibrium between dimethoxymethane, formaldehyde, and methanol.

10. The system of claim 9 wherein the second reaction and separation station includes a catalytic reaction vessel followed by a distillation column.

11. The system of claim 10 wherein the acid catalyst also promotes reaction between dimethoxymethane, poly(dimethoxymethane), and formaldehyde to produce poly(dimethoxymethane)$_n$ with n=3-5.

12. The system of claim 1 wherein the third separation station is a distillation column in which dimethoxymethane is separated from alcohols methanol and ethanol.

* * * * *